(12) United States Patent
Lin

(10) Patent No.: US 10,420,388 B2
(45) Date of Patent: Sep. 24, 2019

(54) SMART SHOE, SMART DEVICE AND METHOD FOR SWITCHING FUNCTIONAL AREAS

(71) Applicant: SHENZHEN HENGTE INTELLECTUAL NETWORKING TECHNOLOGY CO., LTD., Shenzhen, Guangdong (CN)

(72) Inventor: Yiqing Lin, Fujian (CN)

(73) Assignee: SHENZHEN HENGTE INTELLECTUAL NETWORKING TECHNOLOGY CO., LTD., Shenzhen, Guangdong (CN)

( * ) Notice: Subject to any disclaimer, the term of this patent is extended or adjusted under 35 U.S.C. 154(b) by 159 days.

(21) Appl. No.: 15/637,203

(22) Filed: Jun. 29, 2017

(65) Prior Publication Data

US 2018/0310662 A1 Nov. 1, 2018

(30) Foreign Application Priority Data

Apr. 27, 2017 (CN) .......................... 2017 1 0285759

(51) Int. Cl.
*A43B 7/04* (2006.01)
*H02J 7/35* (2006.01)
*A43B 3/00* (2006.01)
*A61B 5/11* (2006.01)
(Continued)

(52) U.S. Cl.
CPC .............. *A43B 7/04* (2013.01); *A43B 3/0005* (2013.01); *A61B 5/11* (2013.01); *A61B 5/6807* (2013.01); *G06F 21/32* (2013.01); *H02J 7/35* (2013.01); *G06F 2221/2111* (2013.01)

(58) Field of Classification Search
CPC ....... A43B 7/04; A43B 3/0005; A61B 5/6807; A61B 5/11; H02J 7/35; G06F 21/32; G06F 2221/2111
See application file for complete search history.

(56) References Cited

U.S. PATENT DOCUMENTS 7,886,462 B2 * 2/2011 Shepherd ............... A43B 23/26
36/114
2007/0011919 A1 * 1/2007 Case, Jr. .............. A43B 1/0036
36/132
(Continued)

FOREIGN PATENT DOCUMENTS

CN 204653908 U 9/2015

*Primary Examiner* — Brian Wilson
(74) *Attorney, Agent, or Firm* — Pearne & Gordon LLP

(57) ABSTRACT

Provided are a smart shoe, a smart device and a method for switching functional area. The smart shoe includes a shoe body and a smart device provided on a surface of the shoe body. The smart device includes a processing unit, a locating unit, a communication unit, a solar energy receiving unit and a power supply unit. The locating unit is configured to acquire current position information of the smart shoe and send it to the processing unit. The processing unit sends the received position information to a user terminal or a remote server via the communication unit. The solar energy receiving unit is configured to receive solar energy and converting it into electrical energy which is transferred to the power supply unit. The power supply unit is connected with individual functional units of the smart device to supply the electrical energy to the smart device.

18 Claims, 5 Drawing Sheets

(51) Int. Cl.
*G06F 21/32* (2013.01)
*A61B 5/00* (2006.01)

(56) References Cited

U.S. PATENT DOCUMENTS

| | | | | |
|---|---|---|---|---|
| 2010/0090477 | A1* | 4/2010 | Keating | A43B 3/0005 |
| | | | | 290/1 R |
| 2011/0260857 | A1* | 10/2011 | Hamill | A43B 17/00 |
| | | | | 340/539.13 |
| 2014/0159951 | A1* | 6/2014 | Gou | G01S 19/35 |
| | | | | 342/357.25 |

* cited by examiner

SMART SHOE, SMART DEVICE AND METHOD FOR SWITCHING FUNCTIONAL AREAS

TECHNICAL FIELD

The present invention relates to the technical field of smart wearable articles, and particularly to a smart shoe, a smart device and a method for switching functional areas.

BACKGROUND ART

In the prior art, a smart electronic device is usually combined with a wearable article, to form a smart wearable article. Since the smart electronic device needs to stay in a working state for a long period of time, the power life is relatively short, and the smart electronic device needs to be charged frequently, which is quite inconvenient to users.

DISCLOSURE OF THE INVENTION

In order to overcome the above shortcomings of the prior art, an object of the present invention is to provide a smart shoe, which includes a shoe body and a smart device, with the smart device provided on a surface of the shoe body;
 the smart device includes a processing unit, a locating unit, a communication unit, a solar energy receiving unit and a power supply unit;
 the locating unit is electrically connected with the processing unit, and is configured to acquire current position information of the smart shoe and send the current position information to the processing unit;
 the communication unit is electrically connected with the processing unit, and the processing unit is configured to send the received position information to a user terminal or a remote server via the communication unit;
 the solar energy receiving unit is electrically connected with the power supply unit, and is configured to receive solar energy and convert the solar energy into electrical energy which is transferred to the power supply unit; and
 the power supply unit is connected with individual functional units of the smart device, and is configured to supply the electrical energy to the smart device.

Furthermore, in the above smart shoe, the smart device further includes a housing, a switching unit, a lighting unit and a trigger unit;
 the housing is of a hollow structure, and the housing is provided with an opening;
 the switching unit is provided in the housing and is electrically connected with the processing unit, the switching unit is provided thereon with a plurality of functional areas, and the solar energy receiving unit and the lighting unit are provided at different functional areas;
 the lighting unit is connected with the power supply unit, and is configured to provide safety lighting for sports at night; and
 the trigger unit is electrically connected with the processing unit, and is configured to receive a switching trigger signal and send a switching signal to the processing unit; and the processing unit is configured to control, according to the switching signal sent by the trigger unit, the switching unit to make a different functional area face the opening.

Furthermore, in the above smart shoe, the switching unit includes an inner core, a first magnet and a second magnet;
 the inner core is of a cylinder structure, the inner core is provided thereon with an axial rotation shaft, and the rotation shaft is connected with the housing so that the inner core is rotatable within the housing; the functional areas are provided on the inner core, and as the inner core rotates, different functional areas are made to face the opening; and
 the first magnet is provided on the inner core, the second magnet is provided within the housing, and the processing unit is configured to control the first magnet and the second magnet to attract each other, so as to drive the inner core to rotate in the housing.

Furthermore, in the above smart shoe, the first magnet is a permanent magnet, the second magnet is an electromagnet, the second magnet is electrically connected with the processing unit, and the processing unit is configured to control to have the second magnet energized to attract the first magnet, so as to drive the inner core to rotate in the housing.

Furthermore, in the above smart shoe, the switching unit includes a plurality of the second magnets, the processing unit is configured to control to have different second magnets energized, so that the energized second magnet attracts the first magnet, to drive the inner core to rotate to a different position, so as to make a different functional area on the inner core face the opening.

Furthermore, in the above smart shoe, the switching unit includes an inner core and a small motor;
 the inner core is of a cylinder structure, the inner core is provided thereon with an axial rotation shaft, and the rotation shaft is connected with the housing so that the inner core is rotatable within the housing; the functional areas are provided on the inner core, and as the inner core rotates, different functional areas are made to face the opening; and
 the small motor is provided within the housing and is connected with the rotation shaft, the small motor is further connected with the processing unit, and the processing unit is configured to control the small motor to rotate, so as to drive the inner core to rotate in the housing.

Furthermore, in the above smart shoe, the trigger unit includes a light detection module, and the light detection module is connected with the processing unit and is configured to detect surrounding light intensity and send data of the detected light intensity to the processing unit;
 the processing unit is configured to control, if the received light intensity is below a first preset threshold, the switching unit to make the lighting unit face the opening; and
 the processing unit is configured to control, if the received light intensity is above a second preset threshold, the switching unit to make the solar energy receiving unit face the opening.

Furthermore, in the above smart shoe, the trigger unit includes a trigger button, the trigger button is connected with the processing unit, and the processing unit is configured to control, when detecting that the trigger button is pressed down, the switching unit to switch so as to make a different functional area face the opening.

Furthermore, in the above smart shoe, the trigger unit includes a motion detection module, and the motion detection module is connected with the processing unit, and is configured to detect a current motion state of a user and send data of the detected motion state to the processing unit;
 the processing unit is configured to control, if the received motion state corresponds to a preset switching action, the switching unit to switch so as to make a different functional area face the opening.

Furthermore, in the above smart shoe, the communication unit includes a Bluetooth communication module, the Bluetooth communication module is connected with the processing unit, and the smart shoe communicates with the user terminal wirelessly via the Bluetooth communication module.

Furthermore, in the above smart shoe, the communication unit includes a GSM communication module, the GSM communication module is connected with the processing unit, and the smart shoe communicates with the remote server wirelessly via the GSM communication module.

Furthermore, in the above smart shoe, the smart shoe further includes a help button, the help button is connected with the processing unit, and the processing unit is configured to send a help signal when detecting that the help button is pressed down.

Furthermore, in the above smart shoe, the shoe body includes a shoe tongue and a shielding plate, the shielding plate covers the shoe tongue, one end of the shielding plate is fixedly connected with one side of the shoe body, and the other end of the shielding plate is detachably connected with the other side of the shoe body, and the smart device is provided on the shielding plate.

An embodiment of the present invention further provides a smart wearable article, which includes a wearable article body and a smart device, with the smart device provided on a surface of the wearable article body;

the smart device includes a processing unit, a locating unit, a communication unit, a solar energy receiving unit and a power supply unit;

the locating unit is electrically connected with the processing unit, and is configured to acquire current position information of the smart wearable article and send the current position information to the processing unit;

the communication unit is electrically connected with the processing unit, and the processing unit is configured to send the received position information to a user terminal or a remote server via the communication unit;

the solar energy receiving unit is electrically connected with the power supply unit, and is configured to receive solar energy and convert the solar energy into electrical energy which is transferred to the power supply unit; and the power supply unit is connected with individual functional units of the smart device to supply the electrical energy to the smart device.

Furthermore, in the above smart wearable article, the smart device further includes a housing, a switching unit, a lighting unit and a trigger unit;

the housing is of a hollow structure, and the housing is provided with an opening;

the switching unit is provided in the housing and is electrically connected with the processing unit, the switching unit is provided thereon with a plurality of functional areas, and the solar energy receiving unit and the lighting unit are provided at different functional areas;

the lighting unit is connected with the power supply unit, and is configured to provide safety lighting for sports at night; and the trigger unit is electrically connected with the processing unit, and is configured to receive a switching trigger signal and send a switching signal to the processing unit; and the processing unit is configured to control, according to the switching signal sent by the trigger unit, the switching unit to make a different functional area face the opening.

Furthermore, in the above smart wearable article, the switching unit includes an inner core, a first magnet and a second magnet;

the inner core is of a cylinder structure, the inner core is provided thereon with an axial rotation shaft, and the rotation shaft is connected with the housing so that the inner core is rotatable within the housing; the functional areas are provided on the inner core, and as the inner core rotates, different functional areas are made to face the opening; and the first magnet is provided on the inner core, the second magnet is provided within the housing, and the processing unit is configured to control the first magnet and the second magnet to attract each other, so as to drive the inner core to rotate in the housing.

Furthermore, in the above smart wearable article, the first magnet is a permanent magnet, the second magnet is an electromagnet, and the second magnet is electrically connected with the processing unit; the processing unit is configured to control to have the second magnet energized, to attract the first magnet, so as to drive the inner core to rotate in the housing.

Furthermore, in the above smart wearable article, the trigger unit includes a light detection module, and the light detection module is connected with the processing unit and is configured to detect surrounding light intensity and send data of the detected light intensity to the processing unit;

the processing unit is configured to control, if the received light intensity is below a first preset threshold, the switching unit to make the lighting unit face the opening; and the processing unit is configured to control, if the received light intensity is above a second preset threshold, the switching unit to make the solar energy receiving unit face the opening.

Furthermore, in the above smart wearable article, the trigger unit includes a trigger button, the trigger button is connected with the processing unit, and the processing unit is configured to control, when detecting that the trigger button is pressed down, the switching unit to switch so as to make a different functional area face the opening.

Furthermore, in the above smart wearable article, the trigger unit includes a motion detection module, and the motion detection module is connected with the processing unit, and is configured to detect a current motion state of a user and send data of the detected motion state to the processing unit;

the processing unit is configured to control, if the received motion state corresponds to a preset switching action, the switching unit to switch so as to make a different functional area face the opening.

Compared with the prior art, the present invention has the following beneficial effects:

in the smart shoe, the smart device and the method for switching functional areas provided by the embodiments of the present invention, with the provision of the solar energy receiving unit, the solar energy is received for supplying power to the smart shoe or the smart device. In this way, the power life of the smart shoe or the smart device is improved, and the frequency of manual charging is accordingly reduced.

BRIEF DESCRIPTION OF DRAWINGS

In order to more clearly illustrate technical solutions of the embodiments of the present invention, figures which are needed for the embodiments will be introduced briefly below. It should be understood that the figures below merely show some embodiments of the present invention, and therefore should not be considered as limiting the scope. A person ordinarily skilled in the art can also obtain other relevant figures in light of these figures, without paying inventive effort.

Figure 1:
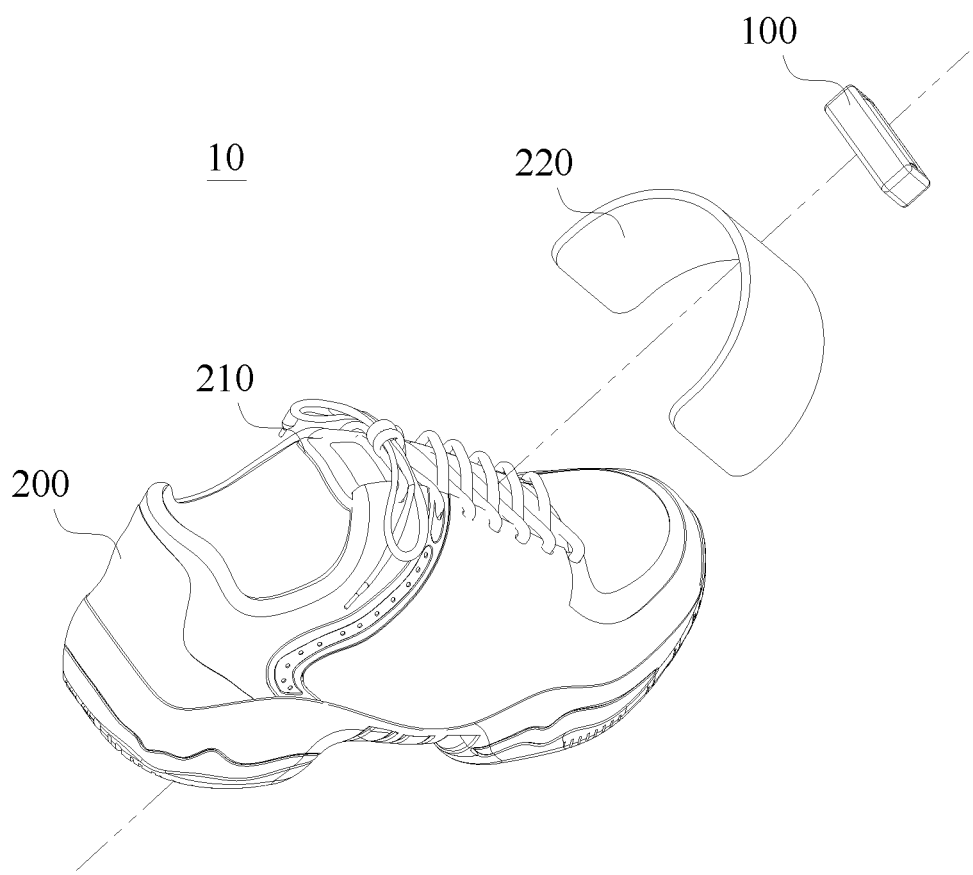
FIG. 1 is a schematic view of a smart shoe provided by an embodiment of the present invention.

Reference signs: 10—smart shoe; 100—smart device; 110—processing unit; 120—locating unit; 130—communication unit; 140—power supply unit; 150—solar energy receiving unit; 160—switching unit; 161—functional area; 1611—first functional area; 1612—second functional area; 162—inner core; 163—rotation shaft; 164—first magnet; 165—second magnet; 166—center of gravity; 170—housing; 171—opening; 180—trigger unit; 200—shoe body; 210—shoe tongue; 220—shielding plate.

DETAILED DESCRIPTION OF EMBODIMENTS

In order to make more clear the objects, the technical solutions and the advantages of the present invention, below the technical solutions of the embodiments of the present invention will be described clearly and completely in conjunction with the figures of the embodiments of the present invention. Apparently, some but not all embodiments of the present invention are described. Generally, components in the embodiments of the present invention, as described and shown in the figures herein, can be arranged and designed in various different configurations.

Therefore, the detailed description below of the embodiments of the present invention as provided in the figures is not intended to limit the scope of protection of the present invention, but merely represents chosen embodiments of the present invention. Based on the embodiments of the present invention, all the other embodiments, which a person ordinarily skilled in the art obtains without paying inventive effort, would fall within the scope of protection of the present invention.

It should be noted that similar reference signs and letters represent similar items in the following figures. Therefore, once a certain item is defined in one figure, it is not needed to be further defined or explained in subsequent figures.

In the description of the present invention, it should be noted that orientational or positional relationships indicated by terms, such as "center", "upper", "lower", "left", "right", "vertical", "horizontal", "inner", and "outer", are based on the orientational or positional relationships as shown in the figures, or the orientational or positional relationships with which the inventive product is conventionally placed, merely for facilitating describing the present invention and simplifying the description, rather than indicating or suggesting that the referred devices or elements have to be in a specific orientation or configured and operated in a specific orientation, and therefore, they should not be construed as limiting the present invention. Besides, terms such as "first", "second" and "third" are merely for descriptive purpose, but should not be understood as indicating or suggesting relative importance.

Besides, terms such as "horizontal", "vertical" and "suspended" do not require the referred component to be absolutely horizontal or suspended, but can be slightly inclined. For example, "horizontal" merely means that its direction is more horizontal compared with "vertical", rather than meaning that this structure has to be completely horizontal, indeed, it can be slightly inclined.

In the description of the present invention, it also should be indicated that unless otherwise specified and defined, terms "arrangement", "installation", "link" and "connection" should be understood in a wide sense. For example, it may be a fixed connection, a detachable connection, or an integrated connection; it may be a mechanical connection, or an electrical connection; it may be a direct connection, or an indirect connection through an intermediate medium; and it may be an inner communication between two elements. For a person ordinarily skilled in the art, the specific meanings of the above mentioned terms in the present invention can be understood according to the specific circumstances.

First Embodiment

Referring to FIG. 1, a preferable embodiment of the present invention provides a smart shoe 10, which includes a shoe body 200 and a smart device 100, with the smart device 100 provided on a surface of the shoe body 200.

Specifically, the shoe body 200 includes a shoe tongue 210 and a shielding plate 220. The shielding plate 220 covers the shoe tongue 210. One end of the shielding plate 220 is fixedly connected with one side of the shoe body 200, and the other end of the shielding plate 210 is detachably connected with the other side of the shoe body 200. The smart device 100 is provided on the shielding plate 200.

Figure 2:
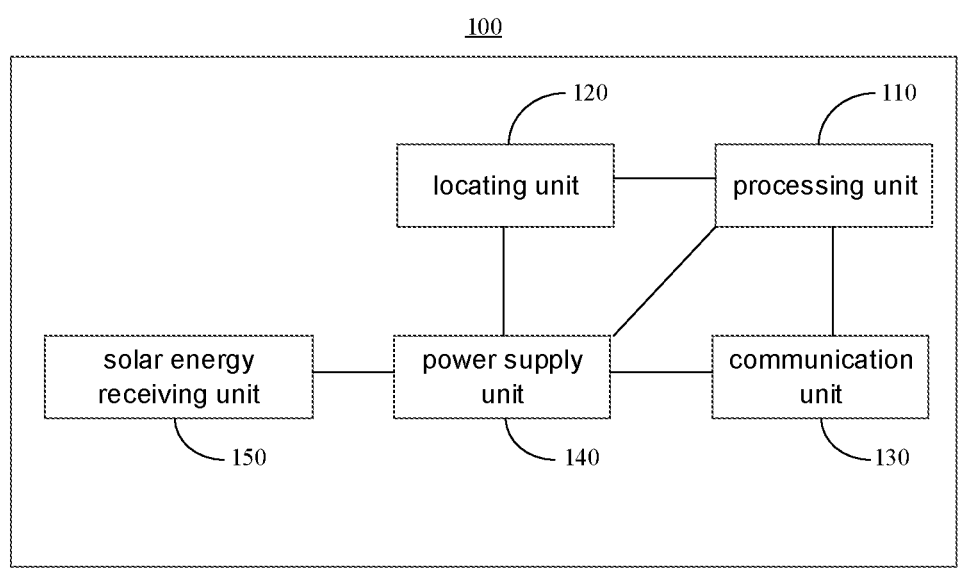
FIG. 2 is a first circuit schematic view of a smart device provided by an embodiment of the present invention.

Referring to FIG. 2, the smart device 100 may include a processing unit 110, a locating unit 120, a communication unit 130, a solar energy receiving unit 150 and a power supply unit 140.

The locating unit 120 is electrically connected with the processing unit 110, and is configured to acquire current position information of the smart shoe 10 and send the current position information to the processing unit 110.

Optionally, in the present embodiment, the locating unit 120 may include, but is not limited just to, a Beidou locating module, a GSM locating module, a GPS locating module and a WIFI locating module, so as to precisely determine a current position of a user.

The communication unit 130 is electrically connected with the processing unit 110. The processing unit 110 sends the received position information to a user terminal or a remote server via the communication unit 130.

Optionally, in the present embodiment, the communication unit 130 may include a Bluetooth communication module. The Bluetooth communication module is connected with the processing unit 110, and the smart shoe 10 communicates with the user terminal wirelessly via the Bluetooth communication module. The user terminal may include, but is not limited just to, a cellphone, a tablet computer and a personal computer. For example, the smart shoe 10 may send, via the communication unit 130, the position information, a motion state and the like of the user to the user terminal for display. A control command sent by the user terminal also may be received via the communication unit 130, to set various functions of the smart shoe 10.

Optionally, in the present embodiment, the communication unit 130 can include a GSM communication module. The GSM communication module is connected with the processing unit 110, and the smart shoe 10 communicates with the remote server wirelessly via the GSM communication module. For example, the smart shoe 10 may directly send information of the user, such as the position information and motion state, to the remote server via the communication unit 130.

The solar energy receiving unit 150 is electrically connected with the power supply unit 140, and is configured to receive solar energy and converting the solar energy into electrical energy which is transferred to the power supply unit 140.

The power supply unit 140 is connected with individual functional units of the smart device 100, and is configured to supply the electrical energy to the smart device 100.

The power supply unit 140 may include a storage battery, and the solar energy received by the solar energy receiving unit 150 is used to charge the storage battery.

Based on the above design, since the solar energy receiving unit 150 converts the solar energy into electrical energy to supply power to the smart shoe 10, the standby time of the smart shoe 10 may be effectively prolonged, reducing the frequency of manual charging, and providing convenient use for users.

Figure 3:
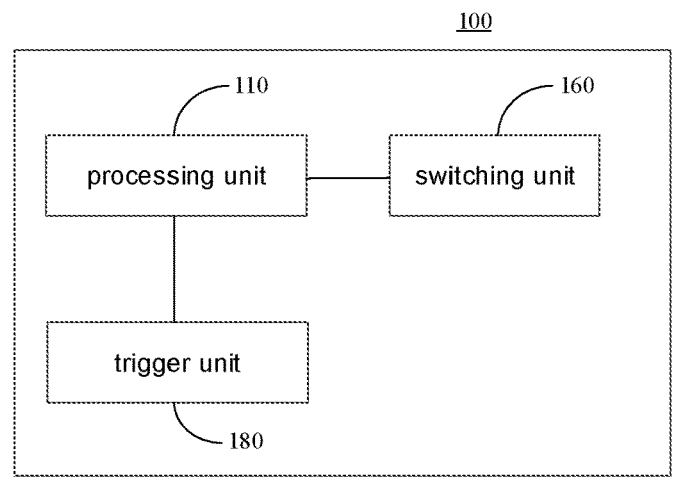
FIG. 3 is a second circuit schematic view of the smart device provided by an embodiment of the present invention.
Figure 4:
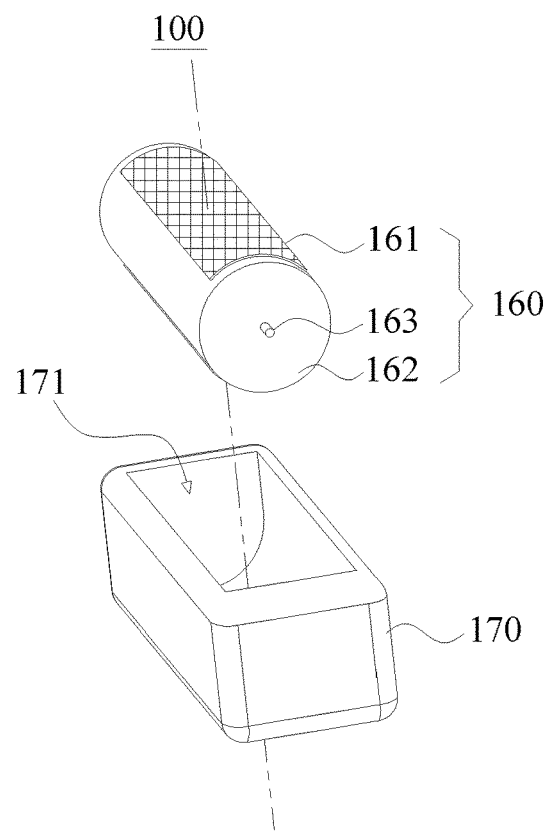
FIG. 4 is a schematic view of the structure of a switching unit provided by an embodiment of the present invention.

Specifically, referring to FIG. 3 and FIG. 4, in the present embodiment, the smart device 100 further includes a housing 170, a switching unit 160, a lighting unit (not shown) and a trigger unit 180.

The housing 170 is of a hollow structure, and the housing 170 is provided with an opening 171.

The switching unit 160 is provided in the housing 170, and is electrically connected with the processing unit 110. The switching unit 160 is provided thereon with a plurality of functional areas 161, and the solar energy receiving unit 150 and the lighting unit are provided at different functional areas 161.

Furthermore, the switching unit 160 includes an inner core 162. The inner core 162 is of a cylinder structure. The inner core 162 is provided thereon with an axial rotation shaft 163. The rotation shaft 163 is connected with the housing 170 so that the inner core 162 is rotatable within the housing 170. The functional areas 161 are provided on the inner core 162. As the inner core 162 rotates, different functional areas 161 are made to face the opening 171.

The lighting unit is connected with the power supply unit 140, and is configured to provide safety lighting for sports at night. The lighting unit is illuminated when it is switched to face the opening 171, and is turned off when it is switched to not face the opening 171.

The trigger unit 180 is electrically connected with the processing unit 110, and is configured to receive a switching trigger signal and send a switching signal to the processing unit 110. The processing unit 110 controls, according to the switching signal sent by the trigger unit 180, the switching unit 160 to make a different functional area face the opening 171.

In a practical application, the solar energy receiving unit 150 and the lighting unit generally will not be used simultaneously, thus the solar energy receiving unit 150 and the lighting unit may be provided at different functional areas 161 of the switching unit 160. In a scene of good light, the solar energy receiving unit 150 may be switched to receive the solar energy so as to supply power to the smart shoe 10. In a scene of poor light, the lighting unit may be switched to provide safety lighting for sports at night.

Based on the above design, different functional units may be provided on different functional areas 161 of the switching unit 160, and thus may be used through switching of the switching unit 160, which reduces the overall space occupied by the individual functional units, thereby reducing the overall volume of the smart device 100, and the influence on the user's motion.

Figure 5:
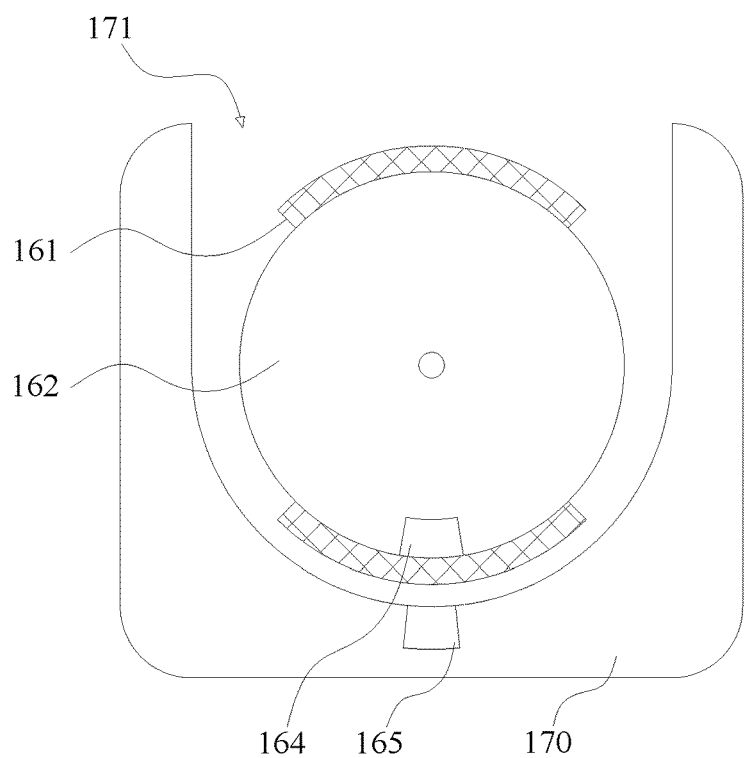
FIG. 5 is a first schematic view of the switching unit provided by the embodiment of the present invention.

Furthermore, referring to FIG. 5, in a first implementation of the present embodiment, the switching unit 160 further includes a first magnet 164 and a second magnet 165. The first magnet 164 is provided on the inner core 162, the second magnet 165 is provided within the housing 170. The processing unit 110 controls the second magnet 165 to attract the first magnet 164, so that the first magnet 164 drives the inner core 162 to rotate in the housing 170.

Specifically, the first magnet 164 is a permanent magnet, the second magnet 165 is an electromagnet, and the second magnet 165 is electrically connected with the processing unit 110. The processing unit 110 is configured to control to have the second magnet 165 energized, to attract the first magnet 164, so as to drive the inner core 162 to rotate in the housing 170.

Figure 6:
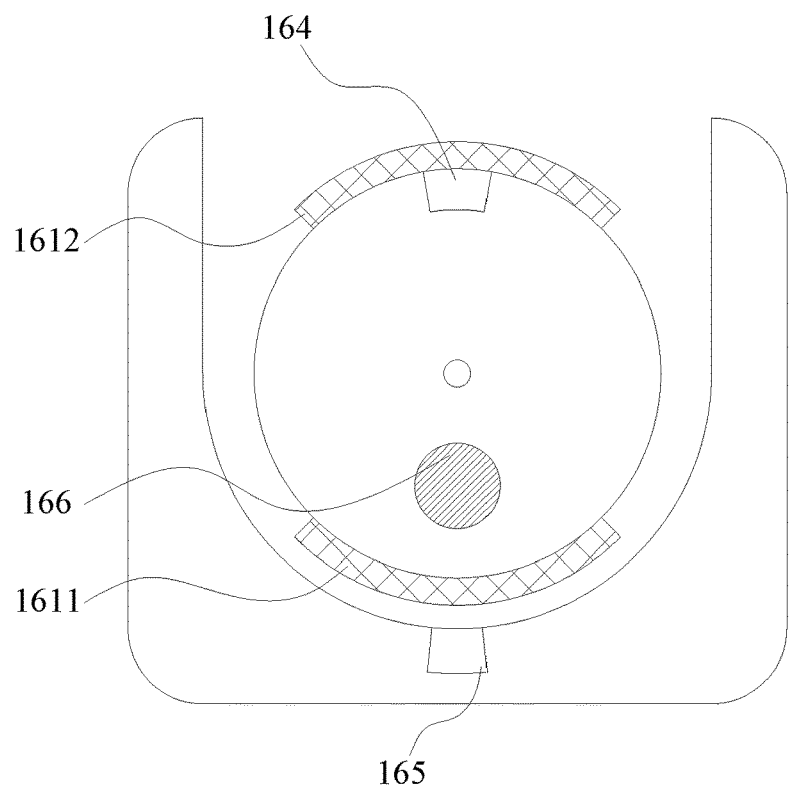
FIG. 6 is a second schematic view of the switching unit provided by the embodiment of the present invention.

Optionally, referring to FIG. 6, in the present embodiment, the functional areas 161 may include a first functional area 1611 and a second functional area 1612, and the first functional area 1611 and the second functional area 1612 may be provided at two opposite sides of an outside surface of the inner core 162. Taking a case where the opening 171 is in a vertical direction as an example, the center of gravity 166 of the inner core 162 may be made deviate to the first functional area 1611, and the first magnet 164 is provided within the inner core 162 and located at a side close to the second functional area 1612. When the second magnet 165 is not energized, the second functional area 1612 is made to face the opening 171 due to the effect of gravity. Once the second magnet 165 is energized, the first magnet 164 is attracted and thus is rotated to approach the second magnet 165, so that the first functional area 1611 is made to face the opening 171.

Figure 7:
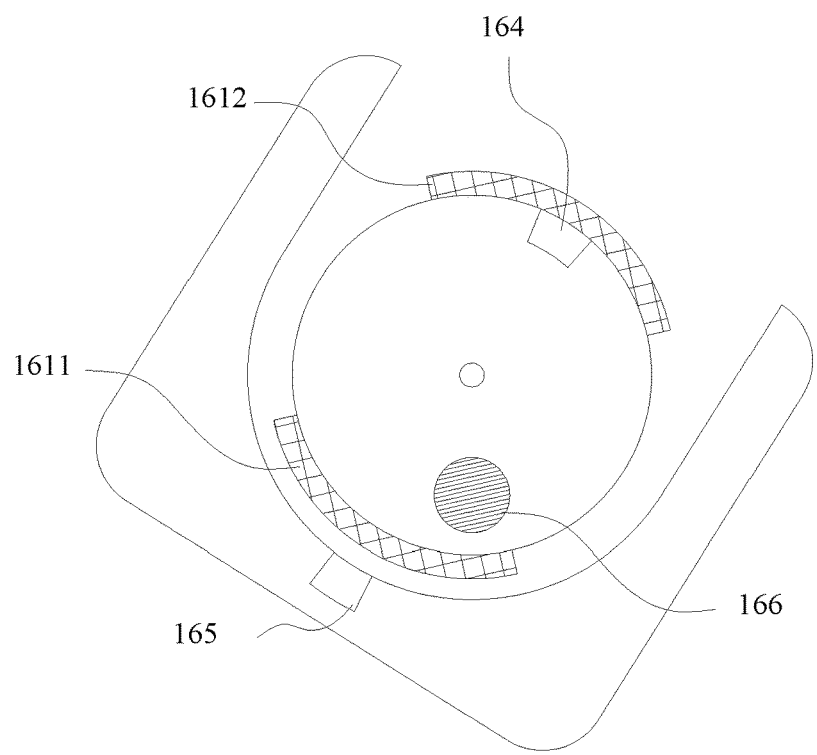
FIG. 7 is a third schematic view of the switching unit provided by the embodiment of the present invention.

It is worth noting that the position arrangement of the center of gravity 166 as described above is merely one implementation of the present embodiment. Depending on the actual spatial orientation of the opening 171, the center of gravity 166 may be provided at different positions relative to the functional areas 161 (e.g., as shown in FIG. 7), so that one of the functional areas 161 may be made to face the opening 171 when the second magnet 165 is not energized.

Figure 8:
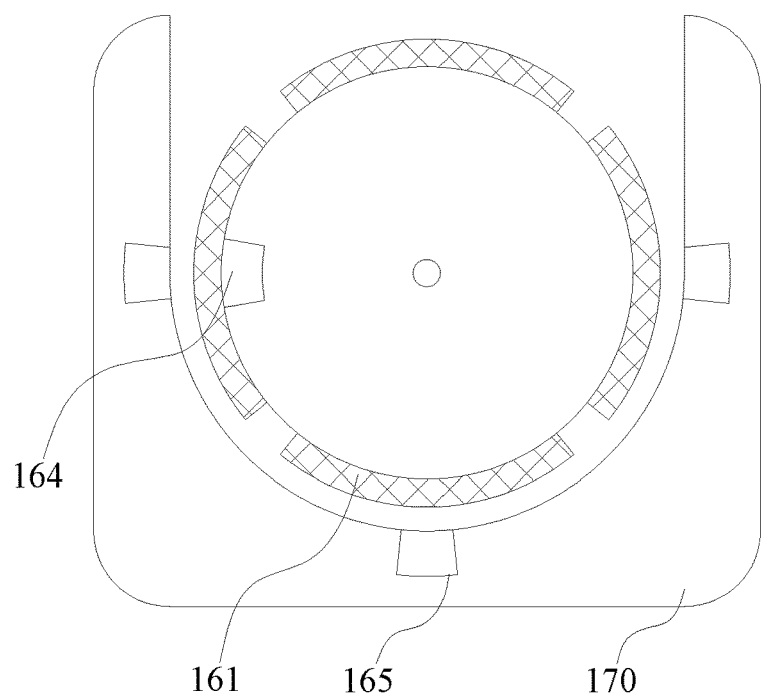
FIG. 8 is a fourth schematic view of the switching unit provided by the embodiment of the present invention.

Optionally, referring to FIG. 8, in the present embodiment, more functional areas 161 may be provided on the switching unit 160. For example, a plurality of lighting units with different degrees of brightness or colors may be provided. In this case, the switching unit 160 may include a plurality of second magnets 165. The processing unit 110 is configured to control to have different second magnets 165 energized, so that the energized second magnet 165 attracts the first magnet 164, to drive the inner core 162 to rotate to a different position, so as to make a different functional area 161 on the inner core 162 face the opening 171.

In another implementation of the present embodiment, a small motor is provided within the housing 170 and is connected with the rotation shaft 163. The small motor is further connected with the processing unit 110, and the processing unit 110 controls the small motor to rotate, so as to drive the inner core 162 to rotate in the housing 170.

Optionally, in the present embodiment, the trigger unit 180 may include a light detection module. The light detection module is connected with the processing unit 110, and is configured to detect surrounding light intensity and send data of the detected light intensity to the processing unit 110.

The processing unit 110 controls the switching unit 160 to switch according to the received light intensity.

For example, if the received light intensity is below a first preset threshold, the processing unit 110 controls the switching unit 160 to make the functional area where the lighting unit is located face the opening 171. If the received light intensity is above a second preset threshold, the processing unit 110 controls the switching unit 160 to make the functional area where the solar energy receiving unit 150 is located face the opening 171. In this way, different functional modules may be automatically switched for use, according to different light intensities.

Optionally, in the present embodiment, the trigger unit 180 may include a trigger button, and the trigger button is connected with the processing unit 110. The processing unit 110 controls, when detecting that the trigger button is pressed down, the switching unit 160 to switch so as to make a different functional area 161 face the opening 171. In this way, the user can manually switch different functional units for use.

Optionally, in the present embodiment, the trigger unit 180 may include a motion detection module. The motion detection module is connected with the processing unit 110, and is configured to detect the current motion state of the user, and send data of the detected motion state to the processing unit 110. If the received motion state corresponds to a preset switching action, the processing unit 110 controls the switching unit 160 to switch so as to make a different functional area 161 face the opening 171.

In the present embodiment, the motion detection module sends the motion state obtained through detection to the processing unit 110. The processing unit 110 determines whether the received motion state corresponds to a stored preset action. If the motion state corresponds to the preset action, the processing unit 110 controls the switching unit 160 to switch.

Optionally, in the present embodiment, the motion detection module may include a gyroscope, an acceleration sensor or a geomagnetic sensor. The gyroscope, the acceleration sensor or the geomagnetic sensor may be separate chips, or may also be integrated into be one chip.

The preset action may be set as a non-conventional action, so as to prevent switching of the switching unit 160 from being triggered by a normal motion. The preset action may be set to include an action type, action duration or action times.

Since front-and-back or up-and-down motions mostly occur during the normal movement of foot, in the present embodiment, the preset action may be set as shaking the shoe left and right.

Optionally, in another implementation of the present embodiment, the processing unit 110 controls, upon each detection of the preset action, the switching unit 160 to switch among the functional areas 161 once so as to make one functional area 161 face the opening 171.

For example, if the smart device 100 includes three functional areas 161, the processing unit 110 controls, upon each detection of shaking of the shoe in the left and right direction, the switching unit 160 to switch among the three functional areas 161 once, so as to make the three functional areas 161 in turn face the opening 171.

Optionally, in another implementation of the present embodiment, the processing unit 110 has records of the preset actions corresponding to different functional areas 161. For example, preset action A corresponds to a functional area 161A, preset action B corresponds to a functional area 161B, and preset action C corresponds to a functional area 161C.

The processing unit 110 controls the switching unit 160 to make the functional area 161 corresponding to the preset action face the opening 171. For example, the processing unit 110 controls, upon detection of preset action A, the switching unit 160 to make the functional area 161A face the opening 171. The processing unit 110 controls, upon detection of preset action C, the switching unit 160 to make the functional area 161C face the opening 171.

Optionally, in the present embodiment, the smart device 100 further includes a help button, and the help button is connected with the processing unit 110. The processing unit 110 sends a help signal when detecting that the help button is pressed down. The help signal may include the current position information of the smart device 100.

Second Embodiment

The present embodiment further provides a smart device 100. Referring to FIG. 2 again, the smart device 100 includes a processing unit 110, a locating unit 120, a communication unit 130, a solar energy receiving unit 150 and a power supply unit 140.

The locating unit 120 is electrically connected with the processing unit 110, and is configured to acquire current position information of the smart device 100 and send the current position information to the processing unit 110.

The communication unit 130 is electrically connected with the processing unit 110, and the processing unit 110 is configured to send the received position information to a user terminal or a remote server via the communication unit 130.

The solar energy receiving unit 150 is electrically connected with the power supply unit 140, and is configured to receive solar energy and converting the solar energy into electrical energy which is transferred to the power supply unit 140.

The power supply unit 140 is connected with individual functional units of the smart device 100 to supply the electrical energy to the smart device 100.

Furthermore, referring to FIG. 3 and FIG. 4 again, in the present embodiment, the smart device 100 further includes a housing 170, a switching unit 160, a lighting unit and a trigger unit 180.

The housing 170 is of a hollow structure, and the housing 170 is provided with an opening 171.

The switching unit 160 is provided in the housing 170, and is electrically connected with the processing unit 110. The switching unit 160 is provided thereon with a plurality of functional areas 161, and the solar energy receiving unit 150 and the lighting unit are provided at different functional areas 161.

The lighting unit is connected with the power supply unit 140, and is configured to provide safety lighting for sports at night.

The trigger unit 180 is electrically connected with the processing unit 110, and is configured to receive a trigger signal and send a switching signal to the processing unit 110. The processing unit 110 is configured to control, according to the switching signal received from the trigger unit 180, the switching unit 160 to make a different functional area 161 face the opening 171.

Furthermore, referring to FIG. 5 again, in the present embodiment, the switching unit 160 includes an inner core 162, a first magnet 164 and a second magnet 165.

The inner core 162 is of a cylinder structure, and the inner core 162 is provided thereon with an axial rotation shaft 163. The rotation shaft 163 is connected with the housing 170, so that the inner core 162 is rotatable in the housing 170. The functional areas 161 are provided on the inner core 162, and as the inner core 162 rotates, different functional areas 161 are made to face the opening 171.

The first magnet 164 is provided on the inner core 162, and the second magnet 165 is provided within the housing 170. The processing unit 110 controls the first magnet 164 and the second magnet 165 to attract each other, so as to drive the inner core 162 to rotate in the housing 170.

Furthermore, in the present embodiment, the first magnet 164 is a permanent magnet, the second magnet 165 is an electromagnet, and the second magnet 165 is electrically connected with the processing unit 110. The processing unit 110 is configured to control to have the second magnet 165 energized, to attract the first magnet 164, so as to drive the inner core 162 to rotate in the housing 170.

Furthermore, in the present embodiment, the trigger unit 180 may include a light detection module. The light detection module is connected with the processing unit 110, and is configured to detect surrounding light intensity and send data of the detected light intensity data to the processing unit 110.

The processing unit 110 is configured to control, if the received light intensity is below a first preset threshold, the switching unit 160 to make the functional area where the lighting unit is located face the opening 171.

The processing unit 110 is configured to control, if the received light intensity is above a second preset threshold, the switching unit 160 to make the functional area where the solar energy receiving unit 150 is located face the opening 171.

Furthermore, in the present embodiment, the trigger unit 180 may include a trigger button, and the trigger button is connected with the processing unit 110. The processing unit 110 is configured to control, when detecting that the trigger button is pressed down, the switching unit 160 to switch so as to make a different functional area 161 face the opening 171.

Furthermore, in the present embodiment, the trigger unit 180 may include a motion detection module. The motion detection module is connected with the processing unit 110, and is configured to detect a current motion state of the user, and send data of the detected motion state to the processing unit 110.

If the received motion state corresponds to a preset switching action, the processing unit 110 controls the switching unit 160 to switch so as to make a different functional area 161 face the opening 171.

Third Embodiment

Figure 9:
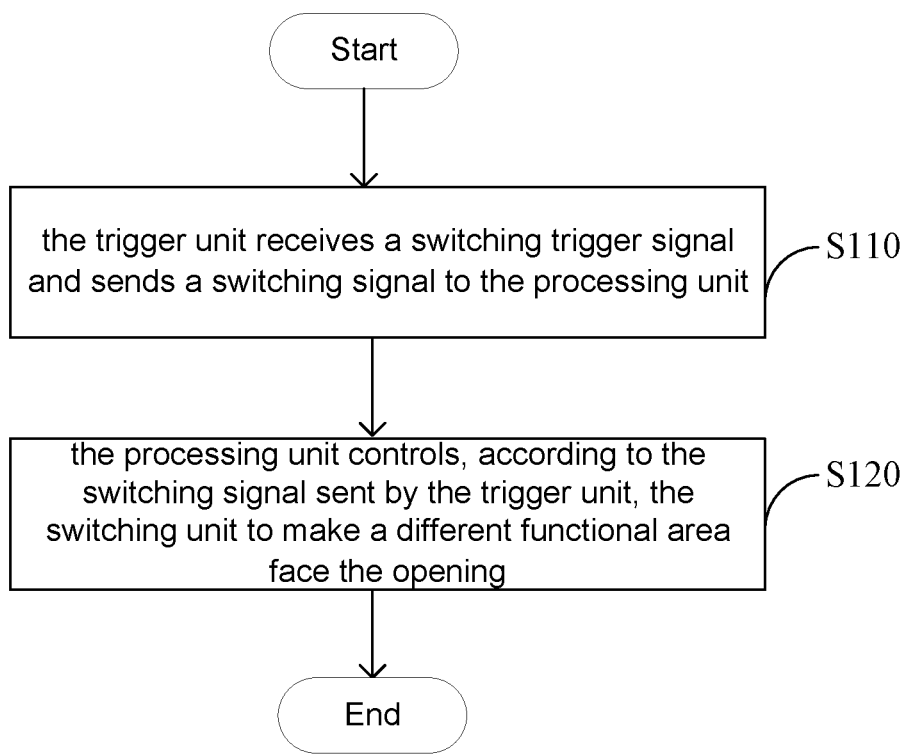
FIG. 9 is a flow chart schematically showing steps of a method for switching functional areas provided by an embodiment of the present invention.

The present embodiment provides a method for switching functional modules. The method may be applied to the smart device 100 provided by the second embodiment. Referring to FIG. 9, below steps of the method are explained in detail.

In step S110, the trigger unit 180 receives a switching trigger signal and sends a switching signal to the processing unit 110.

In step S120, the processing unit 110 controls, according to the switching signal sent by the trigger unit 180, the switching unit 160 to make a different functional area 161 face the opening 117.

In a first implementation of the present embodiment, the trigger unit 180 may include a light detection module, and the light detection module is connected with the processing unit 110 and is configured to detect surrounding light intensity.

If the received light intensity is below a first preset threshold, the processing unit 110 controls the switching unit 160 to make a functional area where the lighting unit is located face the opening 171.

If the received light intensity is above a second preset threshold, the processing unit 110 controls the switching unit 160 to make a functional area where the solar energy receiving unit 150 is located face the opening 171.

In a second implementation of the present embodiment, the trigger unit 180 includes a trigger button, and the trigger button is connected with the processing unit 110.

When detecting that the trigger button is pressed down, the processing unit 110 controls the switching unit 160 to switch so as to make a different functional area 161 face the opening 171.

In a third implementation of the present embodiment, the trigger unit 180 may include a motion detection module. The motion detection module is connected with the processing unit 110, and is configured to detect a current motion state of the user.

If the received motion state corresponds to a preset switching action, the processing unit 110 controls the switching unit 160 to switch so as to make a different functional area 161 face the opening 171.

To sum up, in the smart shoe 10, the smart device 100 and the method for switching functional areas provided by the embodiments of the present invention, with the provision of the solar energy receiving unit 150, the solar energy is received for supplying power to the smart shoe 10 or the smart device 100. In this way, the power life of the smart shoe 10 or the smart device 100 is improved, and the frequency of manual charging is accordingly reduced.

In the embodiments provided in the present application, it should be understood that the disclosed devices and method also can be realized in other manners. The device embodiments described above are merely illustrative. For example, the flow chart and the block diagrams in the drawings show implementable system architectures, functions and operations of the device, method and computer program product according to of the multiple embodiments of the present invention. In this regard, each block in the flow chart or the block diagrams may represent a module, a program segment or a part of code, and such module, program segment or part of code contains one or more executable commands for realizing a specified logical function. It also should be noted that, in some alternative implementations, the functions indicated in the blocks also can take place in an order different from that indicated in the figures. For example, steps indicated by two successive blocks actually can be substantially performed in parallel, and sometimes they also can be performed in an inverse order, depending on the related functions. It also should be noted that each block in the block diagrams and/or flow chart and combinations of the blocks in the block diagrams and/or flow chart can be realized with a dedicated hardware-based system performing the specified function or action, or can be realized with a combination of dedicated hardware and computer commands.

Besides, various functional modules in the various embodiments of the present invention can be integrated together to form one independent part, or the various modules also can each be independent, and two or more modules also can be integrated to form one independent part.

It should be indicated that, relational terms, such as first and second, of the specification are merely used to distinguish one entity or operation from another entity or operation, but do not necessarily require or suggest that these entities or operations have any such practical relationship or order therebetween. Moreover, terms, such as "include", "contain" or any other variants thereof, intend to be non-excluding, so that a process, method, article or device including a series of elements includes not only those elements, but also other elements which are not specifically listed, or also elements inherent to such process, method, article or device. In the case of no more limitations, an element defined by a statement " . . . including(s) a . . . " does not exclude the case where another same element also exists in the process, method, article or device including the element.

The foregoing are merely specific implementations of the present invention, and the scope of protection of the present invention is not limited thereto. Any variations or substitutions, which would readily occur to any skilled person familiar with the present technical field within the scope of the technology disclosed by the present invention, should fall into the scope of protection of the present invention. Therefore, the protection scope of the present invention should be defined by the scope of protection of the claims.

The invention claimed is:

1. A smart shoe, comprising a shoe body and a smart device, wherein the smart device is provided on a surface of the shoe body;
   the smart device comprises a processing unit, a locating unit, a communication unit, a solar energy receiving unit and a power supply unit;
   the locating unit is electrically connected with the processing unit, and is configured to acquire current position information of the smart shoe and send the current position information to the processing unit;
   the communication unit is electrically connected with the processing unit, and the processing unit is configured to send the received position information to a user terminal or a remote server via the communication unit;
   the solar energy receiving unit is electrically connected with the power supply unit, and is configured to receive solar energy and convert the solar energy into electrical energy which is transferred to the power supply unit; and
   the power supply unit is connected with individual functional units of the smart device, and is configured to supply the electrical energy to the smart device,
   wherein the smart device further comprises a housing, a switching unit, a lighting unit and a trigger unit;
   the housing is of a hollow structure, and the housing is provided with an opening;
   the switching unit is provided in the housing and is electrically connected with the processing unit, the switching unit is provided thereon with a plurality of functional areas, and the solar energy receiving unit and the lighting unit are provided at different functional areas of the plurality of functional areas;
   the lighting unit is connected with the power supply unit, and is configured to provide safety lighting for sports at night; and
   the trigger unit is electrically connected with the processing unit, and is configured to receive a switching trigger signal and send a switching signal to the processing unit and the processing unit is configured to control, according to the switching signal sent by the trigger unit, the switching unit to make a different functional area of the plurality of functional areas face the opening.

2. The smart shoe according to claim 1, wherein the switching unit comprises an inner core, a first magnet and a second magnet;
   the inner core is of a cylinder structure, the inner core is provided thereon with an axial rotation shaft, and the rotation shaft is connected with the housing so that the inner core is rotatable within the housing; the plurality of functional areas are provided on the inner core, and as the inner core rotates, a different functional areas of the plurality of functional areas is made to face the opening; and
   the first magnet is provided on the inner core, the second magnet is provided within the housing, and the processing unit is configured to control the first magnet and the second magnet to attract each other, so as to drive the inner core to rotate in the housing.

3. The smart shoe according to claim 2, wherein the first magnet is a permanent magnet, the second magnet is an electromagnet, the second magnet is electrically connected with the processing unit, and the processing unit is configured to control to have the second magnet energized, to attract the first magnet, so as to drive the inner core to rotate in the housing.

4. The smart shoe according to claim 3, wherein the switching unit comprises a plurality of the second magnets, the processing unit is configured to control to have different second magnets energized, so that the energized second magnet attracts the first magnet, to drive the inner core to rotate to a different position, so as to make a different functional area of the plurality of functional areas on the inner core face the opening.

5. The smart shoe according to claim 1, wherein the switching unit comprises an inner core and a small motor;
   the inner core is of a cylinder structure, the inner core is provided thereon with an axial rotation shaft, and the rotation shaft is connected with the housing so that the inner core is rotatable within the housing; the plurality of functional areas is provided on the inner core, and as the inner core rotates, a different functional areas of the plurality of functional areas is made to face the opening; and
   the small motor is provided within the housing and is connected with the rotation shaft, the small motor is further connected with the processing unit, and the processing unit is configured to control the small motor to rotate, so as to drive the inner core to rotate in the housing.

6. The smart shoe according to claim 1, wherein the trigger unit comprises a light detection module, and the light detection module is connected with the processing unit and is configured to detect surrounding light intensity and send data of the detected light intensity to the processing unit;
   the processing unit is configured to control, if the received light intensity is below a first preset threshold, the switching unit to make the lighting unit face the opening; and the processing unit is configured to control, if the received light intensity is above a second preset threshold, the switching unit to make the solar energy receiving unit face the opening.

7. The smart shoe according to claim 1, wherein the trigger unit comprises a trigger button, the trigger button is connected with the processing unit, and the processing unit is configured to control, when detecting that the trigger button is pressed down, the switching unit to switch so as to make a different functional area of the plurality of functional areas face the opening.

8. The smart shoe according to claim 1, wherein the trigger unit comprises a motion detection module, and the motion detection module is connected with the processing unit, and is configured to detect a current motion state of a user and send data of the detected motion state to the processing unit;

the processing unit is configured to control, if the received motion state corresponds to a preset switching action, the switching unit to switch so as to make a different functional area of the plurality of functional areas face the opening.

9. The smart shoe according to claim 1, wherein the communication unit comprises a Bluetooth communication module, the Bluetooth communication module is connected with the processing unit, and the smart shoe communicates with the user terminal wirelessly via the Bluetooth communication module.

10. The smart shoe according to claim 1, wherein the communication unit comprises a GSM communication module, the GSM communication module is connected with the processing unit, and the smart shoe communicates with the remote server wirelessly via the GSM communication module.

11. The smart shoe according to claim 1, wherein the smart shoe further comprises a help button, the help button is connected with the processing unit, and the processing unit is configured to send a help signal when detecting that the help button is pressed down.

12. The smart shoe according to claim 1, wherein the shoe body comprises a shoe tongue and a shielding plate, the shielding plate covers the shoe tongue, one end of the shielding plate is fixedly connected with one side of the shoe body, and the other end of the shielding plate is detachably connected with the other side of the shoe body, and the smart device is provided on the shielding plate.

13. A smart device, comprising a processing unit, a locating unit, a communication unit, a solar energy receiving unit and a power supply unit;

wherein the locating unit is electrically connected with the processing unit, and is configured to acquire current position information of the smart device and send the current position information to the processing unit;

the communication unit is electrically connected with the processing unit, and the processing unit is configured to send the received position information to a user terminal or a remote server via the communication unit;

the solar energy receiving unit is electrically connected with the power supply unit, and is configured to receive solar energy and convert the solar energy into electrical energy which is transferred to the power supply unit; and the power supply unit is connected with individual functional units of the smart device to supply the electrical energy to the smart device wherein the smart device further comprises a housing, a switching unit, a lighting unit and a trigger unit the housing is of a hollow structure, and the housing is provided with an opening;

the switching unit is provided in the housing and is electrically connected with the processing unit, the switching unit is provided thereon with a plurality of functional areas, and the solar energy receiving unit and the lighting unit are provided at different functional areas of the plurality of functional areas;

the lighting unit is connected with the power supply unit, and is configured to provide safety lighting for sports at night; and the trigger unit is electrically connected with the processing unit, and is configured to receive a switching trigger signal and send a switching signal to the processing unit and the processing unit is configured to control, according to the switching signal sent by the trigger unit, the switching unit to make a different functional area of the plurality of functional areas face the opening.

14. The smart device according to claim 13, wherein the switching unit comprises an inner core, a first magnet and a second magnet;

the inner core is of a cylinder structure, the inner core is provided thereon with an axial rotation shaft, and the rotation shaft is connected with the housing so that the inner core is rotatable within the housing; the plurality of functional areas are provided on the inner core, and as the inner core rotates, a different functional areas of the plurality of functional areas is made to face the opening; and the first magnet is provided on the inner core, the second magnet is provided within the housing, and the processing unit is configured to control the first magnet and the second magnet to attract each other, so as to drive the inner core to rotate in the housing.

15. A method for switching functional areas of the plurality of functional areas, applicable to the smart device according to claim 13, wherein the method comprises:

the trigger unit receiving the switching trigger signal and sending the switching signal to the processing unit; and the processing unit controlling, according to the switching signal sent by the trigger unit, the switching unit to make a different functional area of the plurality of functional areas face the opening.

16. The method according to claim 15, wherein the trigger unit comprises a light detection module, and the light detection module is connected with the processing unit and is configured to detect surrounding light intensity; the step of the processing unit controlling, according to the switching signal sent by the trigger unit, the switching unit to make a different functional area of the plurality of functional areas face the opening comprises:

the processing unit controlling, if the received light intensity is below a first preset threshold, the switching unit to make the lighting unit face the opening;

the processing unit controlling, if the received light intensity is above a second preset threshold, the switching unit to make the solar energy receiving unit face the opening.

17. The method according to claim 15, wherein the trigger unit comprises a trigger button, the trigger button is connected with the processing unit, and the step of the processing unit controlling, according to the switching signal sent by the trigger unit, the switching unit to make a different functional area of the plurality of functional areas face the opening comprises:

the processing unit controlling, when detecting that the trigger button is pressed down, the switching unit to switch so as to make a different functional area of the plurality of functional areas face the opening.

18. The method according to claim 15, wherein the trigger unit comprises a motion detection module, the motion detection module is connected with the processing unit and is configured to detect a current motion state of a user, and the step of the processing unit controlling, according to the switching signal sent by the trigger unit, the switching unit to make a different functional area of the plurality of functional areas face the opening comprises:

the processing unit controlling, if the received motion state corresponds to a preset switching action, the switching unit to switch so as to make a different functional area of the plurality of functional areas face the opening.

* * * * *